(12) United States Patent
Sharkey et al.

(10) Patent No.: US 11,351,035 B2
(45) Date of Patent: ***Jun. 7, 2022

(54) OSTEOARTHRITIS TREATMENT AND DEVICE

(71) Applicant: ZIMMER KNEE CREATIONS, INC., Exton, PA (US)

(72) Inventors: Peter F. Sharkey, Villanova, PA (US); Charles F. Leinberry, Chester Springs, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/018,451

(22) Filed: Sep. 11, 2020

(65) Prior Publication Data

US 2020/0405493 A1 Dec. 31, 2020

Related U.S. Application Data

(60) Continuation of application No. 16/225,756, filed on Dec. 19, 2018, now Pat. No. 10,792,159, which is a (Continued)

(51) Int. Cl.
*A61F 2/38* (2006.01)
*A61F 2/28* (2006.01)
(Continued)

(52) U.S. Cl.
CPC ............... *A61F 2/38* (2013.01); *A61B 5/055* (2013.01); *A61B 5/4504* (2013.01);
(Continued)

(58) Field of Classification Search
CPC .............. A61F 2/389; A61F 2002/2835; A61F 2002/2892
See application file for complete search history.

(56) References Cited

U.S. PATENT DOCUMENTS 5,273,964 A 12/1993 Lemons
5,514,137 A 5/1996 Coutts
(Continued)

FOREIGN PATENT DOCUMENTS

| RU | 2161929 C1 | 1/2001 |
| WO | WO-2004080384 A2 | 9/2004 |
| WO | WO-2005107614 A1 | 11/2005 |

OTHER PUBLICATIONS

"U.S. Appl. No. 12/110,434, Examiner Interview Summary dated Mar. 21, 2011", 3 pgs.
(Continued)

*Primary Examiner* — Javier G Blanco
(74) *Attorney, Agent, or Firm* — Schwegman Lundberg & Woessner, P.A.

(57) ABSTRACT

A method for treating arthritis of a joint includes identifying a bone lesion in a bone adjacent to the joint; and implanting in the bone a reinforcing member in or adjacent to the bone lesion. A kit for conducting the method includes: (a) at least one reinforcing member having a proximal face adapted to face the joint, a distal face adapted to face away from the joint, and a wedge-shaped edge adapted to pierce bone, wherein the at least one reinforcing member is planar and sterile; and (b) a container adapted to maintain the at least one reinforcing member sterile. Another kit includes: (a) a sterile fluid; (b) a syringe for injecting the fluid into a bone; (c) a curing agent adapted to cure the fluid to polymerize and/or cross-link; and (d) a container adapted to maintain the sterility of contents of the container.

12 Claims, 1 Drawing Sheet

Related U.S. Application Data continuation of application No. 15/945,403, filed on Apr. 4, 2018, now Pat. No. 10,182,916, which is a continuation of application No. 15/668,898, filed on Aug. 4, 2017, now Pat. No. 9,956,082, which is a continuation of application No. 15/470,017, filed on Mar. 27, 2017, now Pat. No. 9,757,239, which is a continuation of application No. 14/461,656, filed on Aug. 18, 2014, now Pat. No. 9,636,161, which is a continuation of application No. 14/138,262, filed on Dec. 23, 2013, now Pat. No. 8,998,998, which is a continuation of application No. 13/269,136, filed on Oct. 7, 2011, now abandoned, which is a division of application No. 12/110,434, filed on Apr. 28, 2008, now Pat. No. 8,062,364.

(60) Provisional application No. 60/914,465, filed on Apr. 27, 2007.

(51) Int. Cl.

| | | |
|---|---|---|
| *A61B 17/68* | (2006.01) | |
| *A61L 27/12* | (2006.01) | |
| *A61L 27/50* | (2006.01) | |
| *A61B 5/055* | (2006.01) | |
| *A61B 5/00* | (2006.01) | |
| *A61B 17/88* | (2006.01) | |
| *A61L 24/02* | (2006.01) | |
| *A61B 17/00* | (2006.01) | |

(52) U.S. Cl.
CPC ............ *A61B 5/4585* (2013.01); *A61B 17/68* (2013.01); *A61B 17/8805* (2013.01); *A61B 17/8811* (2013.01); *A61B 17/8825* (2013.01); *A61F 2/28* (2013.01); *A61F 2/389* (2013.01); *A61L 24/02* (2013.01); *A61L 27/12* (2013.01); *A61L 27/50* (2013.01); *A61B 2017/00933* (2013.01); *A61F 2002/2817* (2013.01); *A61F 2002/2835* (2013.01); *A61F 2002/2892* (2013.01); *A61F 2310/00023* (2013.01); *A61F 2310/00131* (2013.01); *A61L 2400/06* (2013.01); *A61L 2430/02* (2013.01); *Y10S 623/908* (2013.01)

(56) References Cited

U.S. PATENT DOCUMENTS

| | | | |
|---|---|---|---|
| 5,556,429 A | 9/1996 | Felt | |
| 5,755,809 A | 5/1998 | Cohen et al. | |
| 5,902,825 A | 5/1999 | Jia | |
| 6,140,452 A | 10/2000 | Felt et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,280,474 B1 | 8/2001 | Cassidy et al. | |
| 6,306,177 B1 | 10/2001 | Felt et al. | |
| 6,395,007 B1 | 5/2002 | Bhatnagar et al. | |
| 6,527,810 B2 | 3/2003 | Johnson et al. | |
| 6,564,083 B2 | 5/2003 | Stevens | |
| 6,607,561 B2 | 8/2003 | Brannon | |
| 6,613,054 B2 | 9/2003 | Scribner et al. | |
| 6,692,526 B1 | 2/2004 | Snyder et al. | |
| 6,711,432 B1 | 3/2004 | Krause et al. | |
| 6,719,761 B1 | 4/2004 | Reiley et al. | |
| 6,746,451 B2 | 6/2004 | Middleton et al. | |
| 6,767,369 B2 | 7/2004 | Boyer, II et al. | |
| 6,818,018 B1 | 11/2004 | Sawhney | |
| 6,827,720 B2 | 12/2004 | Leali | |
| 6,863,899 B2 | 3/2005 | Koblish et al. | |
| 6,887,246 B2 | 5/2005 | Bhatnagar et al. | |
| 7,153,307 B2 | 12/2006 | Scribner | |
| 7,166,570 B2 | 1/2007 | Hunter et al. | |
| 7,261,720 B2 | 8/2007 | Stevens et al. | |
| 7,425,549 B2 | 9/2008 | Little et al. | |
| 7,442,195 B1 | 10/2008 | Behrens | |
| 7,708,742 B2 | 5/2010 | Scribner et al. | |
| 7,771,431 B2 | 8/2010 | Scribner et al. | |
| 7,811,290 B2 | 10/2010 | Rabiner | |
| 8,062,364 B1 | 11/2011 | Sharkey et al. | |
| 8,152,813 B2 | 4/2012 | Osorio et al. | |
| 8,168,692 B2 | 5/2012 | Wenz | |
| 8,551,178 B2 | 10/2013 | Sharkey et al. | |
| 8,574,303 B2 | 11/2013 | Sharkey et al. | |
| 8,882,848 B2 | 11/2014 | Sharkey et al. | |
| 8,998,998 B2 | 4/2015 | Sharkey et al. | |
| 9,283,014 B2 | 3/2016 | Sharkey et al. | |
| 9,439,703 B1 | 9/2016 | Sharkey et al. | |
| 9,636,161 B2 | 5/2017 | Sharkey et al. | |
| 9,757,239 B2 | 9/2017 | Sharkey et al. | |
| 9,956,082 B2 | 5/2018 | Sharkey et al. | |
| 10,182,916 B2 | 1/2019 | Sharkey et al. | |
| 2003/0055316 A1 | 3/2003 | Brannon | |
| 2003/0055431 A1 | 3/2003 | Brannon | |
| 2003/0135214 A1 | 7/2003 | Fetto | |
| 2003/0138473 A1 | 7/2003 | Koblish et al. | |
| 2005/0101673 A1 | 5/2005 | Norden | |
| 2005/0119219 A1 | 6/2005 | Bellini et al. | |
| 2005/0177169 A1 | 8/2005 | Fisher et al. | |
| 2005/0251266 A1 | 11/2005 | Maspero et al. | |
| 2006/0057184 A1 | 3/2006 | Nyez et al. | |
| 2006/0064164 A1 | 3/2006 | Thelen et al. | |
| 2006/0172934 A1 | 8/2006 | Nycz et al. | |
| 2007/0010440 A1 | 1/2007 | Schense et al. | |
| 2007/0016163 A1 | 1/2007 | Santini et al. | |
| 2007/0123894 A1 | 5/2007 | Claypool et al. | |
| 2007/0233135 A1 | 10/2007 | Gil et al. | |
| 2007/0259018 A1 | 11/2007 | Mckay | |
| 2007/0275028 A1 | 11/2007 | Barry et al. | |
| 2007/0287988 A1 | 12/2007 | Trebing et al. | |
| 2008/0031915 A1 | 2/2008 | Becerra et al. | |
| 2008/0113008 A1 | 5/2008 | Roche | |
| 2008/0154311 A1 | 6/2008 | Staeubli | |
| 2008/0294085 A1 | 11/2008 | Stamps et al. | |
| 2008/0294269 A1 | 11/2008 | Fell | |
| 2009/0081169 A1 | 3/2009 | Egrise et al. | |
| 2009/0123378 A1 | 5/2009 | Wong et al. | |
| 2010/0076503 A1 | 3/2010 | Beyar et al. | |
| 2010/0145451 A1 | 6/2010 | Dee | |
| 2010/0179549 A1 | 7/2010 | Keller et al. | |
| 2012/0029522 A1 | 2/2012 | Sharkey et al. | |
| 2012/0035609 A1 | 2/2012 | Sharkey et al. | |
| 2014/0107795 A1 | 4/2014 | Sharkey et al. | |
| 2014/0014891 A1 | 5/2014 | Sharkey et al. | |
| 2015/0148909 A1 | 5/2015 | Sharkey et al. | |
| 2015/0238239 A1 | 8/2015 | Sharkey et al. | |
| 2016/0242833 A1 | 8/2016 | Sharkey et al. | |
| 2017/0196695 A1 | 7/2017 | Sharkey et al. | |
| 2017/0354506 A1 | 12/2017 | Sharkey et al. | |
| 2018/0221159 A1 | 8/2018 | Sharkey et al. | |
| 2019/0125540 A1 | 5/2019 | Sharkey et al. | |

OTHER PUBLICATIONS

"U.S. Appl. No. 12/110,434, Examiner Interview Summary dated Nov. 2, 2010", 3 pgs.
"U.S. Appl. No. 12/110,434, Final Office Action dated Feb. 3, 2011", 9 pgs.
"U.S. Appl. No. 12/110,434, Non Final Office Action dated Aug. 20, 2010", 11 pgs.
"U.S. Appl. No. 12/110,434, Notice of Allowance dated Sep. 14, 2011", 14 pgs.
"U.S. Appl. No. 12/110,434, Preliminary Amendment filed Aug. 27, 2009", 7 pgs.
"U.S. Appl. No. 12/110,434, Response filed Mar. 25, 2011 to Final Office Action dated Feb. 3, 2011", 18 pgs.
"U.S. Appl. No. 12/110,434, Response filed Jun. 2, 2010 to Restriction Requirement dated May 7, 2010", 2 pgs.
"U.S. Appl. No. 12/110,434, Response filed Nov. 16, 2010 to Non Final Office Action dated Nov. 2, 2010", 17 pgs.

(56) References Cited

OTHER PUBLICATIONS

"U.S. Appl. No. 12/110,434, Restriction Requirement dated May 7, 2010", 7 pgs.
"U.S. Appl. No. 13/269,136, Advisory Action dated Nov. 8, 2013", 3 pgs.
"U.S. Appl. No. 13/269,136, Final Office Action dated Aug. 28, 2013", 10 pgs.
"U.S. Appl. No. 13/269,136, Non Final Office Action dated Feb. 27, 2014", 10 pgs.
"U.S. Appl. No. 13/269,136, Non Final Office Action dated Mar. 14, 2013", 15 pgs.
"U.S. Appl. No. 13/269,136, Response filed Jun. 14, 2013 to Non Final Office Action dated Mar. 14, 2013", 16 pgs.
"U.S. Appl. No. 13/269,136, Response filed Oct. 25, 2013 to Final Office Action dated Aug. 28, 2013", 12 pgs.
"U.S. Appl. No. 13/269,136, Response filed Nov. 27, 2013 to Advisory Action dated Nov. 8, 2013", 13 pgs.
"U.S. Appl. No. 13/273,903, Non Final Office Action dated Mar. 19, 2014", 12 pgs.
"U.S. Appl. No. 13/273,903, Notice of Allowance dated Aug. 6, 2013", 11 pgs.
"U.S. Appl. No. 13/273,903, Response filed Jun. 19, 2013 to Non Final Office Action dated Mar. 19, 2014", 17 pgs.
"U.S. Appl. No. 13/273,912, 312 Amendment filed Jun. 4, 2013", 6 pgs.
"U.S. Appl. No. 13/273,912, Non Final Office Action dated Oct. 16, 2012", 15 pgs.
"U.S. Appl. No. 13/273,912, Notice of Allowance dated Mar. 25, 2013", 15 pgs.
"U.S. Appl. No. 13/273,912, Notice of Allowance dated Aug. 5, 2013", 13 pgs.
"U.S. Appl. No. 13/273,912, PTO Response to 312 Amendment dated Jul. 16, 2013", 2 pgs.
"U.S. Appl. No. 13/273,912, Response filed Dec. 20, 2012 to Non Final Office Action dated Oct. 16, 2012", 17 pgs.
"U.S. Appl. No. 14/138,262, Non Final Office Action dated Aug. 12, 2014", 14 pgs.
"U.S. Appl. No. 14/138,262, Notice of Allowance dated Jan. 22, 2015", 13 pgs.
"U.S. Appl. No. 14/138,262, Preliminary Amendment filed May 20, 2014", 6 pgs.
"U.S. Appl. No. 14/138,262, Preliminary Amendment filed Dec. 30, 2013", 5 pgs.
"U.S. Appl. No. 14/138,262, Response filed Dec. 12, 2014 to Non-Final Office Action dated Aug. 12, 2014", 14 pgs.
"U.S. Appl. No. 14/169,281, Notice of Allowance dated Sep. 29, 2014", 15 pgs.
"U.S. Appl. No. 14/169,281, Preliminary Amendment filed Feb. 17, 2014", 4 pgs.
"U.S. Appl. No. 14/169,281, Supplemental Preliminary Amendment filed May 20, 2014", 5 pgs.
"U.S. Appl. No. 14/169,281, Supplemental Preliminary Amendment filed May 28, 2014", 6 pgs.
"U.S. Appl. No. 14/169,281, Supplemental Preliminary Amendment filed Aug. 12, 2014", 8 pgs.
"U.S. Appl. No. 14/461,656, Advisory Action dated Apr. 21, 2016", 3 pgs.
"U.S. Appl. No. 14/461,656, Advisory Action dated Nov. 10, 2015", 2 pgs.
"U.S. Appl. No. 14/461,656, Final Office Action dated Feb. 12, 2016", 14 pgs.
"U.S. Appl. No. 14/461,656, Final Office Action dated Aug. 7, 2015", 10 pgs.
"U.S. Appl. No. 14/461,656, Non Final Office Action dated Mar. 12, 2015", 15 pgs.
"U.S. Appl. No. 14/461,656, Non Final Office Action dated Sep. 22, 2016", 17 pgs.
"U.S. Appl. No. 14/461,656, Notice of Allowance dated Dec. 21, 2016", 13 pgs.
"U.S. Appl. No. 14/461,656, Preliminary Amendment, filed Nov. 21, 2014", 7 pgs.
"U.S. Appl. No. 14/461,656, Response filed Apr. 11, 2016 to Final Office Action dated Feb. 12, 2016", 9 pgs.
"U.S. Appl. No. 14/461,656, Response filed Jun. 1, 2015 to Non Final Office Action dated Mar. 12, 2015", 9 pgs.
"U.S. Appl. No. 14/461,656, Response filed Nov. 16, 2016 to Non Final Office Action dated Sep. 22, 2016", 9 pgs.
"U.S. Appl. No. 14/461,656, Supplemental Preliminary Amendment filed Feb. 26, 2015", 5 pgs.
"U.S. Appl. No. 14/461,656. Response filed Oct. 29, 2015 to Final Office Action dated Aug. 7, 2015", 8 pgs.
"U.S. Appl. No. 14/710,750, Non Final Office Action dated Jul. 31, 2015", 16 pgs.
"U.S. Appl. No. 14/710,750, Notice of Allowance dated Feb. 1, 2016", 16 pgs.
"U.S. Appl. No. 14/710,750, Response filed Oct. 29, 2015 to Non Final Office Action dated Jul. 31, 2015", 12 pgs.
"U.S. Appl. No. 15/047,694, Preliminary Amendment filed Feb. 22, 2016", 8 pgs.
"U.S. Appl. No. 15/047,694, Notice of Allowance dated Aug. 10, 2016", 16 pgs.
"U.S. Appl. No. 15/470,017, Notice of Allowance dated Jul. 7, 2017", 16 pgs.
"U.S. Appl. No. 15/470,017, Preliminary Amendment, filed May 3, 2017", 6 pgs.
"U.S. Appl. No. 15/668,898, Notice of Allowance dated Mar. 21, 2018", 13 pgs.
"U.S. Appl. No. 15/668,898, Preliminary Amendment filed Aug. 9, 2017", 7 pgs.
"U.S. Appl. No. 15/668,898, Supplemental Preliminary Amendment Filed Dec. 15, 2017", 8 pgs.
"U.S. Appl. No. 15/945,403, Notice of Allowance dated Sep. 20, 2018", 13 pgs.
"U.S. Appl. No. 15/945,403, Preliminary Amendment filed May 10, 2018", 6 pgs.
"U.S. Appl. No. 16/225,756, Amendment Filed Mar. 13, 2020 to Noice of Allowance dated Dec. 13, 2019", 5 pgs.
"U.S. Appl. No. 16/225,756, Notice of Allowance dated Jun. 2, 2020", 9 pgs.
"U.S. Appl. No. 16/225,756, Notice of Allowance dated Dec. 13, 2019", 14 pgs.
"U.S. Appl. No. 16/225,756, Preliminary Amendment filed Dec. 28, 2018", 5 pgs.
Altman, et al., "Development of Criteria for the Classification and Reporting of Osteoarthritis, Classification of Osteoarthritis in the Knee: Classification of Osteoarthritis of the Knee", Arthritis & Rheumatism 29(8), (Aug. 1986), 1039-1049.
Arnoldi, et al., "Intraosseous Phlebography, Intraosseous Pressure Measurements and 99mTC-Polyphosphate Scintigraphy in Patients with Various Painful Conditions in the Hip and Knee", Acta Orthrop Scand, 51, (1980), 19-28.
Baranyay, et al., "Association of Bone Marrow Lesions with Knee Structures and Risk Factors for Bone Marrow Lesions in the Knees of Clinically Healthy, Community-Based Adults", Seminar in Arthritis & Rheumatism, (Oct. 2007), 112-118.
Bingham, et al., "Risedronate Decreases Biochemical Markers of Cartilage Degradation but Does Not Decrease Symptoms or Slow Radiographic Progression in Patients with Medial Compartment Osteoarthritis of the Knee:Results of the 2-Year Multinational Knee Osteoarthritis Study", Arthritis & Rheumatism 54(11), (Nov. 2006), 3494-3507.
Bollet, "Edema of the bone marrow can cause pain in osteoarthritis and other diseases of bone and joints", Ann Intern Med. 134(7), (Apr. 3, 2001), 591-3.
Buckland-Wright, et al., "A 2 Yr Longitudinal Radiographic Study Examining the Effect of a Bisphosphonate (Risedronate) Upon Subchondral Bone Loss in Osteoarthritic Knee Patients", Rheumatology 46, (2006), 257-264.
Carbone, et al., "The Relationship of Antiresorptive Drug Use to Structural Findings and Symptoms of Knee Osteoarthritis", Arthritis & Rheumatism 50(11), (Nov. 2004), 3516-3525.

(56) References Cited

OTHER PUBLICATIONS

Cicuttini, et al., "Association of Cartilage Defects with Loss of Knee Cartilage in Healthy, Middle-Aged Adults: A Prospective Study", Arthritis & Rheumatism 5 2(7), (Jul. 2005), 2033-2039.

Cicuttini, "Comparison of Tibial Cartilage vol. and Radiologic Grade of the Tibiofemoral Joint", Arthritis & Rheumatism 48(3), (Mar. 2003), 682-688.

Clegg, et al., "Glucosamine, Chondroitin Sulfate, and the Two in Combination for Painful Knee Osteoarthritis", The New England Journal of Medicine 354(8), (Feb. 2006), 795-808.

Felson, et al., "An Update on the Epidemiology of Knee and Hip Osteoarthritis with a View to Prevention", Arthritis & Rheumatism 41(8), (Aug. 1998), 1343-1355.

Felson, et al., "Bone marrow edema and its relation to progression of knee osteoarthritis", Ann Intern Med. 139(5 Pt 1), (Sep. 2, 2003), 330-6.

Felson, et al., "Correlation of the Development of Knee Pain With Enlarging Bone Marrow Lesions on Magnetic Resonance Imaging", Arthritis & Rheumatism 56(9), (Sep. 2007), 2986-2992.

Felson, et al., "Obesity and Knee Osteoarthritis, the Framingham Study", Annals of Internal Medicine 109, (Jul. 1988), 18-24.

Felson, et al., "Osteoarthritis: Is it a Disease of Cartilage or of Bone?", Arthritis & Rheumatism 50(2), (Feb. 2004), 341-344.

Felson, et al., "The association of bone marrow lesions with pain in knee osteoarthritis", Ann Intern Med., (Apr. 3, 2001), 541-9.

Felson, et al., "The Prevalence of Knee Osteoarthritis in the Elderly, The Framingham Osteoarthritis Study", Arthritis and Rheumatism 30(8), (Aug. 1987), 914-918.

Garnero, et al., "Bone Marrow Abnormalities on Magnetic Resonance Imaging Are Associated with Type II Collagen Degradation in Knee Osteoarthritis: A Three-Month Longitudinal Study", Arthritis & Rheumatism 52(9), (Sep. 2005), 2822-2829.

Guymer, et al., "A Study of the Prevalence and Associations of Subchondral Bone Marrow Lesions in the Knees of Healthy, Middle-Aged Women", Osteoarthritis and Cartilage1 5(12), (Dec. 2007), 1437-1442.

Hunter, et al., "Bone marrow lesions from osteoarthritis knees are characterized by sclerotic bone that is less well mineralized", Arthritis Research & Therapy 11 (1), Online Retrieved from the internet: <http://arthritis-research.com/content/U/1/R11>, (Jan. 2009), 9 pgs.

Hunter, et al., "Increase in Bone Marrow Lesions Associated with Cartilage Loss: A Longitudinal Magnetic Resonance Imaging Study of Knee Osteoarthritis", Arthritis & Rheumatism 54(5), (May 2006), 1529-1535.

Jones, et al., "Early Radiographic Osteoarthritis is Associated with Substantial Changes in Cartilage Volume and Tibial Bone Surface Area in Both Males and Females", Osteoarthritis and Cartilage12(2), (Feb. 2004), 169-174.

Mayerhoefer, et al., "Short-term outcome of painful bone marrow oedema of the knee following oral treatment with iloprost or tramadol: results of an exploratory phase II study of 41 patients", Rheumatology 2007, (Jul. 2007), 1-6.

McAlindon, et al., "Magnetic resonance imaging in osteoarthritis of the knee: correlation with radiographic and scintigraphic findings", Ann Rheum Dis. 50, (1991), 14-19.

McQueen, F. M, et al., "A vital clue to deciphering bone pathology: MRI bone oedema in rheumatoid arthritis and osteoarthritis", Annals of the Rheumatic Diseases 2007, 66, (2007), 1549-1552.

Radin, et al., "Role of Subchondral Bone in the Initiation and Progression of Cartilage Damage", Clinical Orthopaedics and Related Research 213, (Dec. 1986), 34-40.

Segal, et al., "Baseline Articular Contact Stress Levels Predict Incident Symptomatic Knee Osteoarthritis Development in the MOST Cohort", Journal of Orthopaedic Research, (Dec. 2009), 1562-1568.

Wang, et al., "Factors Affecting Progression of Knee Cartilage Defects in Normal Subjects Over 2 Years", Rheumatology, 45, (2006), 79-84.

Wilson, et al., "Expression of Glutamate Receptors and Transporters in Human Subchondral Bone in Osteoarthritis", Paper #23, Knee Society Meeting in Boston, MA, (Oct. 2009), 1 pg.

Wluka, et al., "Bone Marrow Lesions Predict Progression of Cartilage Defects and Loss of Cartilage Volume in Healthy Middle-Aged Adults Without Knee Pair Over 2 Years", Rheumatology, (Jul. 2008), 5 pgs.

Wluka, et al., "The Clinical Correlates of Articular Cartilage Defects in Symptomatic Knee Osteoarthritis: A Prospective Study", Rheumatology, 44, (Jul. 2005), 1311-1316.

Zanetti, et al., "Bone Marrow Edema Pattern in Osteoarthritio Knees: Correlation between MR Imaging and Histologic Findings", Radiology, 215, (2000), 835-840.

U.S. Appl. No. 15/047,694 U.S. Pat. No. 9,439,703, filed Feb. 19, 2016, Osteoarthritis Treatment and Device.

U.S. Appl. No. 15/470,017 U.S. Pat. No. 9,757,239, filed Mar. 27, 2017, Osteoarthritis Treatment and Device.

U.S. Appl. No. 15/668,898 U.S. Pat. No. 9,956,082, filed Aug. 4, 2017, Osteoarthritis Treatment and Device.

U.S. Appl. No. 15/945,403 U.S. Pat. No. 10,182,916, filed Apr. 4, 2018, Osteoarthritis Treatment and Device.

U.S. Appl. No. 16/225,756, filed Dec. 19, 2018, Osteoarthritis Treatment and Device.

U.S. Appl. No. 12/110,434 U.S. Pat. No. 8,062,364, filed Apr. 28, 2008, Osteoarthritis Treatment and Device.

U.S. Appl. No. 13/269,136, filed Oct. 7, 2011, Osteoarthritis Treatment and Device.

U.S. Appl. No. 14/138,262 U.S. Pat. No. 8,998,998, filed Dec. 23, 2013, Osteoarthritis Treatment and Device.

U.S. Appl. No. 13/273,912 U.S. Pat. No. 8,574,303, filed Oct. 14, 2011, Osteoarthritis Treatment and Device.

U.S. Appl. No. 13/273,903 U.S. Pat. No. 8,551,178, filed Oct. 14, 2011, Osteoarthritis Treatment and Device.

U.S. Appl. No. 14/169,281 U.S. Pat. No. 8,882,848, filed Jan. 31, 2014, Osteoarthritis Treatment and Device.

U.S. Appl. No. 14/461,656 U.S. Pat. No. 9,636,161, filed Aug. 18, 2014, Osteoarthritis Treatment and Device.

U.S. Appl. No. 14/710,750 U.S. Pat. No. 9,283,014, filed May 13, 2015, Osteoarthritis Treatment and Device.

OSTEOARTHRITIS TREATMENT AND DEVICE

CROSS-REFERENCE TO RELATED APPLICATIONS

This application is a continuation of U.S. patent application Ser. No. 16/225,756, filed on Dec. 19, 2018, which is a continuation of U.S. patent application Ser. No. 15/945,403 filed on Apr. 4, 2018, now issued as U.S. Pat. No. 10,182,916, which is a continuation of U.S. patent application Ser. No. 15/668,898, filed on Aug. 4, 2017, now issued as U.S. Pat. No. 9,956,082, which is a continuation of U.S. patent application Ser. No. 15/470,017 filed on Mar. 27, 2017, now issued as U.S. Pat. No. 9,757,239, which is a continuation of U.S. patent application Ser. No. 14/461,656 filed on Aug. 18, 2014, now issued as U.S. Pat. No. 9,636,161, which is a continuation of U.S. patent application Ser. No. 14/138,262, filed on Dec. 23, 2013, now issued as U.S. Pat. No. 8,998,998, which is a continuation of U.S. patent application Ser. No. 13/269,136 filed on Oct. 7, 2011 and entitled "OSTEOARTHRITIS TREATMENT AND DEVICE," now abandoned, which is a divisional of U.S. patent application Ser. No. 12/110,434, now U.S. Pat. No. 8,062,364, filed on Apr. 28, 2008 and entitled "OSTEOARTHRITIS TREATMENT AND DEVICE," which application claims priority to U.S. Provisional Application No. 60/914,465, filed on Apr. 27, 2007 and entitled "OSTEOARTHRITIS TREATMENT AND DEVICE," the contents of which are herein incorporated by reference in their entirety.

FIELD

This invention relates to a method and device for treating osteoarthritis, particularly osteoarthritis of the knee.

BACKGROUND

Osteoarthritis is the most common form of arthritis, affecting the hands, knees, hips, spine and other joints. Characteristics of osteoarthritis include a loss of cartilage, seen as a reduction in the joint space, and osteophytes (or bone spurs).

Arthritic pain is a leading cause of lost productivity. The cause of arthritic pain is unclear. The amount of cartilage loss correlates poorly with the severity of pain in an afflicted individual. Likewise, radiographic finding such as osteophytes (bone spurs) and thickening of subchondral bone (eburination) do not correlate with the presence or severity of pain.

Bone marrow lesions (or edemas) are very strongly associated with knee arthritis pain (Felson et al., "The association of bone marrow lesions with pain in knee osteoarthritis," Ann Intern led. 2001 Apr. 3, 134(7):541-9) and disease progression (Felson et al., "Bone marrow edema and its relation to progression of knee osteoarthritis." Ann Intern Med. 2003 Sep. 2; 139(5 Pt 1):330-6). See also U.S. Pat. No. 6,564,083 to Stevens, which describes a method of identifying in a patient having joint pain the susceptibility of the patient to developing progressive osteoarthritis or loss of joint space, by determining the presence or absence of bone marrow edema about or of the joint. The determination is preferably made through the use of Magnetic Resonance Imaging (MRI).

The nature and cause of bone marrow lesions is poorly understood. Histologic examination of these lesions demonstrates abnormal bone with areas of fibrosis, osteonecrosis and extensive bone remodeling (Zanetti et al., "Bone Marrow Edema Pattern in Osteoarthritic Knees: Correlation between MR Imaging and Histologic Findings." Radiology. 2000; 215:835-840). It has been suggested that they are related to inflammation (Bollet, "Edema of the bone marrow can cause pain in osteoarthritis and other diseases of bone and joints," Ann Intern Med. 2001 Apr. 3; 134(7):591-3), venous hypertension (Arnoldi et al., "Intraosseous phlebography, intraosseous pressure measurements and 99mTc-polyphosphate scintigraphy in patients with various painful conditions in the hip and knee." Acta Orthrop Scand. 1980; 51:19-28), or impaired arterial blood flow (McAlindon et al., "Magnetic resonance imaging in osteoarthritis of the knee: correlation with radiographic and scintigraphic findings." Ann Rheum. Dis. 1991; 50:14-9. Others have suggested these lesions reflect increased bone stress and microfracture of the bone (see Felson et al. 2003, supra).

Knee arthritis affects millions of people and the pain associated with this disease can be disabling. Patients who initially present with painful knee arthritis are usually treated non-surgically. Non-surgical treatments are modestly effective at temporarily relieving pain, but not risk free. Pharmacologic intervention (i.e., non-steroidal anti-inflammatory drugs) has been reported to be associated with significant complications, such as gastric ulcers, strokes and heart attacks. Steroid or viscosupplement injection may lead to infection. Steroid injections may also have systemic effects such as increased blood sugar and hypertension. Generally speaking non-surgical interventions are most efficacious for early arthritic disease and do not prevent disease progression.

When patients fail non-surgical treatment, surgical intervention is often recommended. Arthroscopic surgery has been shown to have limited effectiveness and has a small role in the management of knee arthritis. More invasive surgical approaches such as high tibial osteotomy and partial or complete knee replacement predictably relieve pain. However, these major operations are also potentially associated with significant morbidity and occasional mortality. These risks along with the limited durability of implantable devices influence patient and physicians to defer surgery until the symptoms become unbearable.

Accordingly, it is desired to provide an effective, surgical treatment of osteoarthritis, and particularly knee arthritis pain. It is further desired that such surgical treatment be less invasive than high tibial osteotomy and partial or complete knee replacement.

All references cited herein are incorporated herein by reference in their entireties.

SUMMARY

Accordingly, a first aspect of the invention comprises a method for treating arthritis of a joint, said method comprising: identifying a bone lesion in a bone adjacent to the joint; and implanting in the bone a reinforcing member in or adjacent to the bone lesion. The reinforcing member as implanted is preferably free of artificial bones to the bone. The method preferably decreases pain associated with arthritis and/or slows the progression of arthritis.

A second aspect of the invention comprises a kit for treating arthritis of a joint, said kit comprising: (a) at least one reinforcing member comprising a proximal face adapted to face the joint, a distal face adapted to face away from the joint, and a wedge-shaped edge adapted pierce bone, wherein the at least one reinforcing member is planar and sterile; and (b) a container adapted to maintain the at least one reinforcing member sterile.

A third aspect of the invention comprises a kit for treating arthritis of a joint, said kit comprising: (a) a sterile fluid; (b) a syringe for injecting the fluid into a bone; (c) a curing agent adapted to cure the fluid to polymerize and/or cross-link; and (d) a container adapted to maintain the sterility of contents of the container.

A fourth aspect of the invention comprises a method for treating arthritis of a joint, said method comprising: (a) identifying a bone lesion in a bone adjacent to the joint; and (b) implanting in the bone a reinforcing member in or adjacent to the bone lesion, wherein the method stabilizes the bone in order to prevent further biomechanical breakdown of the bone and of adjacent meniscal tissues, and alleviates pain in the joint.

BRIEF DESCRIPTION OF THE DRAWINGS

The invention will be described in conjunction with the following drawings in which like reference numeral designate like elements and wherein:

FIG. 2 also includes a side view (D) of the embodiment shown in overhead view (B).

DESCRIPTION OF THE EMBODIMENTS

The invention is based on our theory that bone marrow lesions detected by MRI represent overstressed bone. Bone is continuously fatigued and damaged by everyday activity. However, bone is a living tissue and bone repair occurs in concert. Certain pathological processes, such as loss of joint cartilage, can disturb the equilibrium between bone damage and bone repair. Cartilage protects underlying bone shielding it from stress. In addition, loss of cartilage leads to joint deformity further increasing bone stress. Overstressed bone sustains more damage than repair, which results in pain.

The invention enhances the strength of bone, shielding bone from excessive stress. Strengthening the bone in accordance with the invention shifts the damage/repair equilibrium toward repair. In addition, strengthening the bone reduces, reverses and/or prevents the deformation of overstressed bone, which should relieve pain and slow arthritic disease progression within the underlying bone and adjacent meniscal tissues (cartilage).

The invention provides an additional treatment option for patients suffering with arthritic pain, particularly in the knee. Those individuals who have exhausted nonsurgical care, but are not symptomatic enough or not prepared for other reasons (emotional, financial, etc.) to undergo more major surgical interventions, are ideal for treatment using the present invention. The method of the invention should be considered minor or outpatient surgery. The risk of complications if expected to be significantly less than with major arthritic surgery, such as high tibial osteotomy and partial or total knee replacement. Preferred embodiments of the inventive treatment stabilize the defect in the subchondral (underlying) bone in order to prevent further biomechanical breakdown of the bone and of the adjacent meniscal tissues, and alleviate the corresponding pain in the joint.

Figure 1:
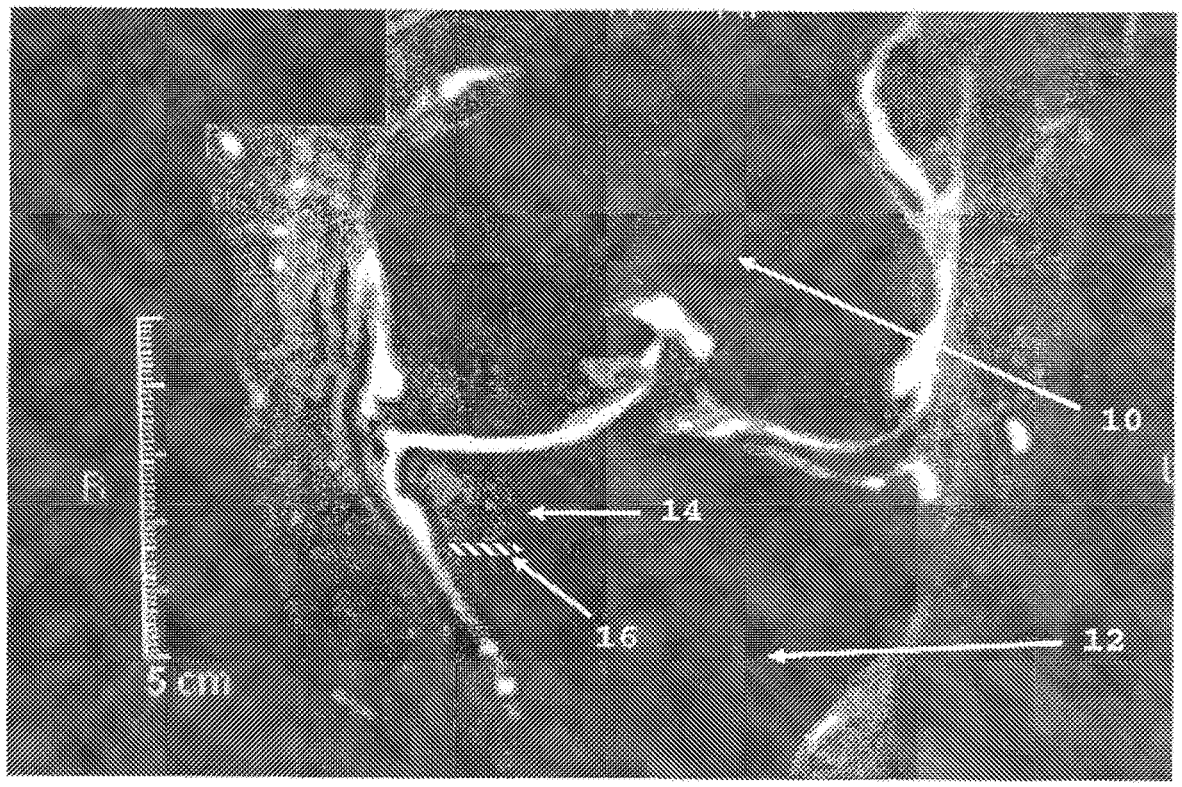
FIG. 1 is a magnetic resonance image (2D IR 1900/90/25.0; COR 200×180; 4.0 FFS; 256×144 pr.) of an arthritic knee on which is overlaid a side view of an embodiment of the reinforcing member of the invention.

The method of the invention comprises identifying a bone lesion in a bone adjacent to the joint, and implanting in the bone a reinforcing member in or adjacent to the bone Lesions. Referring to FIG. 1, an arthritic human knee comprises femur 10 and tibia 12. Bone lesion 14 of tibia 12 presents as a focally increased signal in the marrow in an MRI of the knee. In certain embodiments, coronal spin-echo fat-saturated proton density and T2-weighted fat-saturated magnetic resonance images are preferred. Bone lesions thought to be associated with arthritis are less than 10 cm or 5 cm or 1 cm from the joint. Thus in preferred embodiments, the invention treats bone lesions which are from 0 to 10 cm from the joint, or 0 to 5 cm from the joint, or 0 to 1 cm from the joint.

The bone lesion is preferably identified using MRI, but in less preferred embodiments, other identification means may be employed. For example, bone lesions can be identified using Technetium-99 bone scans, because there is a close correlation between the presence of activity noted on Technetium-99 bone scans and bone marrow lesions. In embodiments of the invention employee MRI, any Mill technology that reveals bone marrow lesions can be used, for example, open MRI, low field strength MRI, extremity MRI, whole body scanner MRI or the like.

Reinforcing member 14 is preferably selected in accordance with the guidance provided by the following bone lesion grading system.

| Bone Lesion Grading System | | |
|---|---|---|
| Class | Bone Lesion Dimension | Comments |
| I | <1 mm | Bone healing is likely and resorbable graft materials are appropriate. Non-limiting exemplary materials for use as the reinforcing member include hyaluronic acid (HA), calcium phosphate (CaP) grafts, and cements (CaP & PMMA). |
| II | 1-3 mm | Bone healing is more challenging and a semi-structural graft material is appropriate. Non-limiting exemplary materials for use as the reinforcing mbmer include HA, CaP, cements (CaP & PMMA), and structural implants of metal and/or polymer. |
| III | 3-5 mm | Bone healing is less likely, and thus structural non-resorbing support is appropriate. Non-limiting exemplary materials for use as the reinforcing member include CaP cements, PMMA cements, and structural implants of metal and/or polymer. |
| IV | >5 mm | Bone healing is unlikely, and thus a permanent structural implant is required. Non-limiting exemplary materials for use as the reinforcing member include PMMA cements, and structural implants of metal and/or polymer. |

FIG. 1 shows a preferred example of how reinforcing member 16 could be implanted in bone lesion 14. It is also within the scope of the invention to implant the reinforcing member adjacent to the bone lesion. For example, the reinforcing member can be implanted adjacent to a side of the bone lesion proximal to the joint and/or adjacent to a side of the bone lesion distal to the joint. One or more than one reinforcing member can be implanted in and/or adjacent to a bone lesion. A reinforcing member is adjacent to a bone lesion if it is less than 10 cm away from an outer surface of the bone lesion. Adjacent reinforcing members can be in contact with an outer surface of the bone lesion. Thus in preferred embodiments, an adjacent reinforcing member can be from 0 to 10 cm from the bone lesions, or 0 to 5 cm from the bone lesion, or 0 to 1 cm from the bone lesion.

It is also preferred that the reinforcing member as implanted be free of bonds to the bone. Thus, the reinforcing member is preferably not, for example, glued, cemented, stapled, stitched, clamped or screwed to the bone. However, the expression "free of artificial bonds to the bone" does not exclude from such embodiments the possibility that bonds are formed by biological processes in situ.

The reinforcing member is implants in the bone in or adjacent the bone lesion such that a proximal face faces the joint and a distal face faces away from the joint. Preferably, the reinforcing member is selected or modified (e.g., cut, torn, etc.) such that a maximum dimension of the proximal face exceeds a maximum dimension of the bone lesion. It is also within the scope of the invention for the maximum dimension of the bone lesion to equal or exceed a maximum dimension of the proximal face. Thus, the reinforcing member can be larger, smaller or the same size as the bone lesion. The reinforcing member is preferably implanted such that the proximal face is perpendicular to a longitudinal axis of the bone. It is preferred that the proximal and/or distal faces be the primary load bearing surfaces.

In certain embodiments, a syringe (optionally with a needle) can be used to inject a fluid into a bone so as to form the reinforcing member in situ. This step can be conducted with or without first creating an opening in the bone. The fluid is preferably a liquid, semi-solid, gel, hydrogel, dispersion or slurry. After injection, the fluid can remain in its originally-injected state, or can cure to a less fluid state. For example, the injected fluid can cross-link or polymerize from a liquid to form a semi-solid, gel or solid. Fluids that cure in situ can be self-curing or can cure in response to curing means, such as, e.g., radiation (e.g., IN light), heat (e.g., body temperature), moisture and/or a curing agent. See, e.g., U.S. Pat. No. 6,818,018 to Sawhney and U.S. Pat. No. 6,280,474 to Cassidy et al.

In certain embodiments, the reinforcing member is a solid or a non-fluid material that is not amenable to injection in to the bone. In these embodiments, the surgeon creates a small opening in the vicinity of the bone lesion. Suitable surgical tools for this task include standard bone instruments (e.g., chisels, etc.) and instruments specifically designed for use in the method of the invention. It is also possible to use the wedge-shaped edge of the reinforcing member to pierce the bone, preferably with assistance from a hammer.

Although it is within the scope of the invention for the surgeon to implant the reinforcing member by studying a previously captured image of the bone lesion and using his or her own senses to estimate the location and boundaries of the bone lesion, it is preferred that the surgeon be provided with additional guidance during surgery. For example, surgery can be conducted using real-time imaging, robotic devices, braces for maintaining the joint in a position consistent with captured images of the joint and/or labels. See, e.g., U.S. Pat. No. 6,711,432 to Krause et al. Suitable labels include but are not limited to radioactive labels, such as Technetium-99 and objects, such as fiducial markers.

Postoperatively, patients may be required to maintain partial weight bearing and use ambulatory aids. Depending upon the physician's direction, full weight bearing may be possible. Routine post intervention physical therapy will likely be required. Additionally, patients will need routine post intervention care, observation and follow-up.

Figure 2:
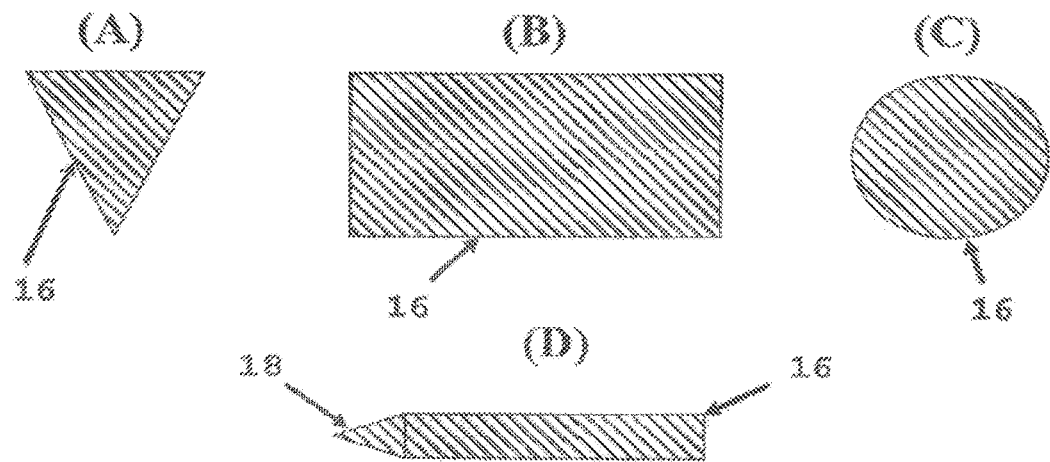
FIG. 2 shows overhead views (A), (B) and (C) of three embodiments of the reinforcing member of the invention.

FIG. 2 shows several different embodiments of reinforcing members of the invention. FIG. 2A shows reinforcing member 16 having a triangular profile, FIG. 2B shows reinforcing member 16 having a rectangular profile and FIG. 2C shows reinforcing member 16 having a circular profile.

Reinforcing member 16 is preferably planar, as seen from FIG. 2D, which shows a side view of the rectangular embodiment of FIG. 2C. The term "planar" as used herein refers to three-dimensional objects which are relatively long in two dimensions and relatively short in a third dimension. Planar reinforcing members in accordance with the invention can have a thickness which is ≤50% of the length and ≤50% of the width of a rectangular reinforcing member (or ≤50% of the diameter in the case of a circular reinforcing member or ≤50% of the height and ≤50% of the base in the case of a triangular reinforcing member).

As can be best seen in FIG. 2D, reinforcing member 16 has wedge-shaped edge 18 on at least one edge thereof. Wedge-shaped edge 18 is adapted to facilitate the step of driving reinforcing member 18 into the bone. Thus, the particular angle and other dimensions of the wedge are dictated by factors that are known in the art. Preferably, wedge-shaped edge 18 is similar to that found on standard surgical tools such as osteotomes or on implants such as blade plates or osteotomy staples.

Reinforcing member 16 comprises a physiologically compatible material that has sufficient durability to reinforce the overstressed bone of the bone lesion and bear physiologic loads. Preferred materials for the reinforcing member include metals, such as titanium, stainless steel, alloys of cobalt and chrome, tantalum, alloys of titanium and nickel and other superelastic metal alloys, such as taught by U.S. Pat. No. 6,527,810. Titanium "foam", tantalum, trabecular metals, nanoceramics or other hightly porous nanomaterials, and chrome cobalt are particularly preferred. Other embodiments comprise the use of bone, such as autografts, allografts, and artificial or synthetic bone substitutes. Certain embodiments comprise the use of polymeric materials.

Reinforcing member 16 is preferably osteogenic, osteoconductive and/or osteoinductive. The term "osteogenic" as used herein refers to the ability of the reinforcing member to promote the growth of new bone tissue. The term "osteoinductive" as used herein refers to the ability of the reinforcing member to recruit cells from the host that have the potential for forming new bone and repairing bone tissue. The term "osteoconductive" as used herein refers to the ability of a non-osteoinductive reinforcing member to serve as a substrate supporting bone growth. Osteoconductive materials that are suitable for use in the present invention are biologically acceptable and include but are not limited to collagen and the various forms of calcium phosphates including hydroxyapatite, tricalcium phosphate, and fluorapatite. Suitable osteoinductive substances include but are not limited to bone morphogenetic proteins (e.g., rhBMP-2), demineralized bone matrix, transforming growth factors (e.g., TGF-beta), osteoblast cells, and various other organic species known to induce bone formation. The osteoconductive and osteoinductive properties may be provided by bone marrow, blood plasma, or morselized bone of the patient, or commercially available materials. Osteoinductive materials such as BMP may be applied to articles of the invention, for example, by immersing the article in an aqueous solution of this material in a dilute suspension of type I collagen. Osteoinductive materials such as TGF-beta may be applied to an article of the invention from a saline solution containing an effective concentration of TGF-beta, or may be carried in the resilient material.

The reinforcing member can be resorbable, but is preferably nonresorbable, particularly when used to treat a chronic condition, such as osteoarthritis.

In certain embodiments, electrical stimulation is applied to the bone to promote bone healing.

The reinforcing member can be provided alone or in a kit according to the invention. A first embodiment of the kit includes at least one reinforcing member, which is sterile, and a container adapted to maintain the sterility of the at least one reinforcing member. Preferably, the containers are sealed flexible bags. The term "sterile" as used herein denotes a condition in which an object has a sterility assurance level (SAL) or $10^{-3}$ or less (preferablye $10^{-6}$ of less) in accordance with current FDA guidelines for medical devices and as measured by AAMI/ISO 11607-1.

The first embodiment of the kid can optionally include an assortment of reinforcing members of various sizes and/or shapes appropriate for use with a variety of bone lesions. The kit can also include instructions for use, e.g., printed on the container and/or on inserts within the container. The kit can still further include a tool for adjusting the size of the reinforcing member, a hammer for driving the reinforcing member into the bone and/or a bone filler to seal the open end of the channel in the bone in which the reinforcing member resides. Suitable bone fillers include but are not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLO-MATRIX made by Wright Medical Technology, Inc.), calcium phosphate (e.g., CALCMON made by Merck &. Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). See U.S. Pat. No. 7,166,570.

A second embodiment of the kit includes a fluid, a syringe for injecting the fluid into a bone and a container adapted to maintain the sterility of the contents of the container. This embodiment of the kit can further comprise a needle and premeasure portions of ingredients in a plurality of separate vials. As with the first embodiment of the kit, this embodiment can optionally include instructions for use, e.g., printed on the container and/or on inserts within the container. The kit can further include bone tools for providing a channel in the bone in which the fluid is injected and/or a bone filler to seal the open end of the channel in the bone in which the reinforcing member resides. The kit can include curing agents (i.e., polymerizing agents, catalysts and/or crosslinking agents) as separate ingredients to be added to the injected fluid. The kit can include other curing means, such as a UV light source or other device for generating radiation. The fluid can be preloaded in the syringe for injection. In some embodiments, a multiple barrel syringe can be included for in situ mixing of ingredients that must be stored separately in different barrels of the syringe (e.g., monomers and polymerizing agent, or polymers and crosslinking agent, etc.).

While the invention is described in the context of osteoarthritis of the knee, it is not limited to such condition. Other conditions that can be treated in accordance with the invention include but are not limited to osteoarthritic of joints other than the knee.

While the invention has been described in detail and with reference to specific examples thereof, it will be apparent to one skilled in the art that various changes and modifications can be made therein without departing from the spirit and scope thereof.

What is claimed is:

1. A method of injecting an injectable fluid material into a targeted treatment area in a subchondral region of a first bone adjacent a joint of a patient for treating a bone marrow lesion identified in the subchondral region, the method comprising:

identifying a bone marrow lesion (BML) in a subchondral region of a first bone adjacent a joint of a patient, the subchondral region of the first bone occurring under an articular surface of the first bone;

creating, in the first bone that contains the bone marrow lesion in the subchondral region, a subchondral injection path to a targeted treatment area for injecting an injectable fluid material into the targeted treatment area, wherein said creating is conducted without creating a void in the targeted treatment area that opens into the overlying articular cartilage of the first bone adjacent the joint so as to preserve an existing condition of the overlying articular cartilage of the first bone adjacent the joint; and injecting an injectable fluid material into the targeted treatment area via the subchondral injection path, wherein the injectable fluid material is resorbable and osteoconductive in the targeted treatment area for supporting new bone growth in the targeted treatment area, and wherein the injectable fluid material is left in the targeted treatment area without also delivering and leaving a solid structural implant in the targeted treatment area in addition to the injectable fluid material, the injectable fluid material comprising a calcium phosphate and hyaluronic acid, where said injecting introduces at least some of the injectable fluid material into defective bone that remains in the identified bone marrow lesion following said creating, wherein said identifying includes identifying the bone marrow lesion through use of magnetic resonance imaging (MRI) of the joint or a Technetium-99 bone scan of the joint.

2. The method of claim 1, wherein the bone marrow lesion is less than 10 cm from the joint.

3. The method of claim 1, wherein the bone marrow lesion is less than 5 cm from the joint.

4. The method of claim 1, wherein the bone marrow lesion is less than 1 cm from the joint.

5. The method of claim 1, wherein the bone marrow lesion is identified through use of magnetic resonance imaging (MRI) of the joint.

6. The method of claim 5, wherein said identifying includes viewing the bone marrow lesion on an MRI of the joint.

7. The method of claim 1, wherein the joint is a knee joint.

8. The method of claim 1, wherein the bone marrow lesion is in a proximal tibia.

9. The method of claim 1, wherein the bone marrow lesion is in a distal femur.

10. The method of claim 1, wherein the joint is other than a knee joint.

11. The method of claim 1, wherein said injecting includes use of a syringe.

12. The method of claim 11, wherein the syringe includes a needle.

* * * * *